United States Patent
Vandenbark et al.

(10) Patent No.: US 7,214,528 B1
(45) Date of Patent: May 8, 2007

(54) DEVICE FOR DIRECT ELECTRICAL DETECTION OF MOLECULES AND MOLECULE-MOLECULE INTERACTIONS

(75) Inventors: Arthur A. Vandenbark, Portland, OR (US); Rajendra Solanki, Portland, OR (US)

(73) Assignee: Oregon Health & Sciences University, Portland, OR (US)

( * ) Notice: Subject to any disclaimer, the term of this patent is extended or adjusted under 35 U.S.C. 154(b) by 396 days.

(21) Appl. No.: 10/335,043

(22) Filed: Dec. 31, 2002

(51) Int. Cl.
*C12M 1/36* (2006.01)
*G01N 15/06* (2006.01)
*C07K 5/00* (2006.01)

(52) U.S. Cl. .............................. 435/283.1; 435/287.2; 422/68.1; 422/82.01; 530/300; 530/350

(58) Field of Classification Search .................. None
See application file for complete search history.

(56) References Cited

U.S. PATENT DOCUMENTS

| | | | |
|---|---|---|---|
| 4,233,144 A * | 11/1980 | Pace et al. ................... 436/544 |
| 4,885,697 A * | 12/1989 | Hubner ........................ 702/27 |
| 5,532,128 A | 7/1996 | Eggers et al. |
| 5,653,939 A | 8/1997 | Hollis et al. |
| 5,670,322 A | 9/1997 | Eggers et al. |
| 5,846,708 A | 12/1998 | Hollis et al. |
| 5,891,630 A | 4/1999 | Eggers et al. |
| 6,169,394 B1 | 1/2001 | Frazier et al. |
| 6,264,825 B1 * | 7/2001 | Blackburn et al. ........ 205/777.5 |
| 6,602,400 B1 * | 8/2003 | Choong et al. ........... 205/777.5 |
| 6,716,620 B2 * | 4/2004 | Bashir et al. ............. 435/287.2 |
| 2002/0090649 A1 | 7/2002 | Chan et al. |

FOREIGN PATENT DOCUMENTS

WO  WO 99/65287  12/1999

OTHER PUBLICATIONS

Schyberg et al., "Impedance analysis of Si/SiO$_2$ structures grafted with biomolecules for the elaboration of an immunosensor," *Sensors and Actuators B*, vol. 26-27, pp. 457-460 (1995).
Bataillard et al., "Direct detection of immunospecies by capacitance measurements," *Analytical Chemistry*, vol. 60, No. 21, pp. 2374-2379 (1988).

* cited by examiner

*Primary Examiner*—B J Forman
(74) *Attorney, Agent, or Firm*—Marger Johnson & McCollom, P.C.

(57) ABSTRACT

An analysis device includes an electrode arrangement, a current/voltage provider, and a circuit analyzer. The electrode arrangement has an interdigitated electrode pair including a first electrode and a second electrode. Coupled to the electrode arrangement is a signal generator adapted to provide a signal (e.g., an alternating current or voltage) having a selected range of frequencies. The analyzer is coupled to the electrode arrangement and is operative to analyze an electrical parameter of the circuit as the signal is applied. An analytic method includes measuring changes in one or more parameters of the circuit over the range of frequencies. By such measurement, the device can determine whether a target moiety has been bound by a probe attached to the electrode(s). The device can also specifically identify the intermolecular system detected, i.e., by "fingerprinting" the electrical response of each molecule or intermolecular complex.

21 Claims, 7 Drawing Sheets

X-AXIS ADDRESS DIODES

DEVICE FOR DIRECT ELECTRICAL DETECTION OF MOLECULES AND MOLECULE-MOLECULE INTERACTIONS

BACKGROUND OF THE INVENTION

The present invention is related to the field of bioelectrical circuit analyzers, and more specifically to bioelectrical circuit analyzers capable of identifying and categorizing various biomolecules and biomolecular complexes by electrical parameter analysis thereof.

Detection of antigens such as viruses and bacteria is critical for medical diagnoses. Currently, the commonly used methods for immunological tests include enzyme-linked immunosorbent assay (ELISA) and immunoradiometric assay (IRMA). However, these multi-step techniques tend to be tedious and expensive. Hence, there is considerable effort directed towards development of microsensors, in particular immunosensors that can allow quick and precise detection of molecules.

Identification of biomolecular complexes also is advantageous in research, e.g. pharmaceutical research and development. As one example, a gene regulatory protein can be identified by its ability to bind to a specific deoxyribonucleic acid sequence. Current methods for detecting such complexes include radiometric, fluorometric and chromogenic assays. Such assays provide only a binary yes-no answer and cannot provide more advanced data, such as differentiation among different binding species.

Electrical detection methods have been based on potentiometric, piezoelectric, and capacitive systems. Potentiometric systems measure the variation in the surface potential of an electrode or change in drain current of a transistor. These measurements tend to be non-specific. Piezoelectric systems measure the change in the mass of molecules bound to a quartz surface, but suffer from instabilities and problems with calibration.

Capacitive measurements have been used for detection of DNA and cell structures, such as U.S. Pat. No. 5,891,630 (Eggers et al.); U.S. Pat. No. 6,169,394 (Frazier et al.); and U.S. Pat. No. 5,846,708 (Hollis et al.). In these studies, the substrates have consisted of $Si/SiO_2$ or metal electrodes coated with insulating material. These approaches further have focused on determination of a unique "resonance frequency" for a given molecule or complex.

Capacitive detection of antibodies and antigens bound to a sensor surface has been reported. However, these electrical detection approaches have employed only a fixed frequency to detect relative changes in the dielectric constant due to binding to the sensor surface.

DETAILED DESCRIPTION OF PREFERRED EMBODIMENT(S)

The present disclosure describes detection of distinguishing characteristics of proteins and other biological compositions using signals spanning frequency ranges of several orders of magnitude.

General Arrangement of System

Figure 1:
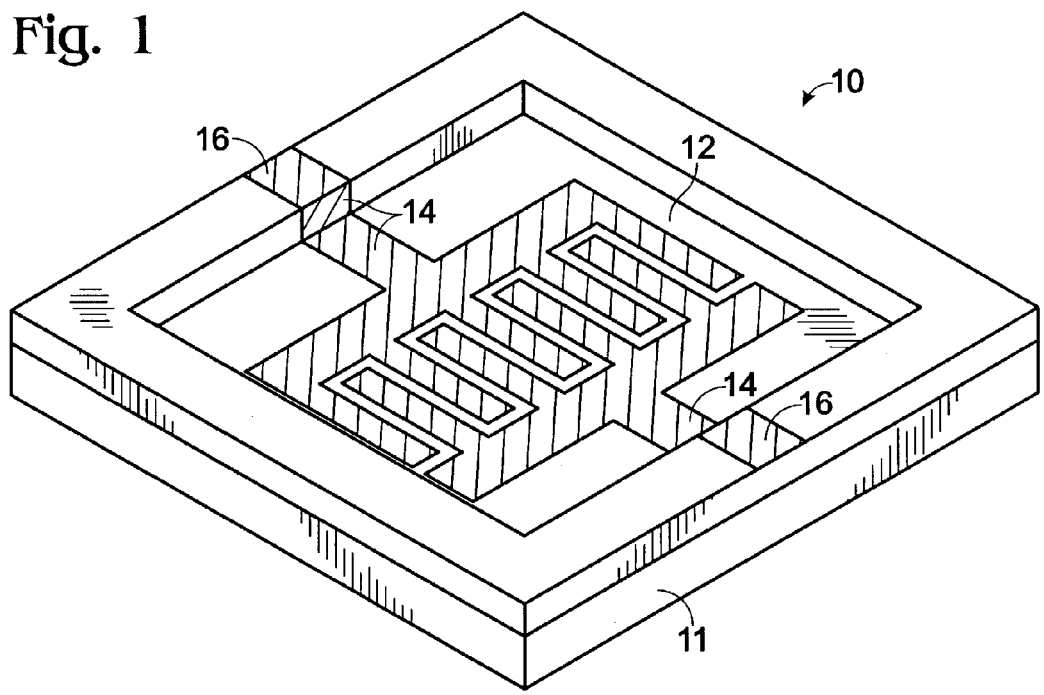
FIG. 1 is a diagram of an electrode module structured to directly detect electrical parameters of a biomolecular electrode.

Turning to FIG. 1, an electrode module 10 for a bioelectrical circuit analyzer 1 includes a substrate 11 with a sample well 12 formed thereon. The sample well 12 is and structured to receive a fluid test sample.

A circuit C (FIG. 3) has metal electrodes 14 positioned in contact with the sample well 12 and formed in an apposed arrangement on the silicon substrate 11. Electrodes 14 preferably have interdigitated fingers 15 (FIG. 2A) to increase the area of the electrodes 14 that are apposed.

The substrate 11 is a semiconductor, preferably constructed of silicon or a dielectric/insulator material. While the substrate 11 may be formed of a semiconductor, it is necessary that the region immediately adjacent the electrodes be insulating relative to the capacitance of the electrodes. This can be accomplished by oxidizing silicon in the regions of the substrate 11 on which the electrodes 14 are deposited.

The metal electrodes 14 are constructed of a material that a biomolecular probe 30 (FIGS. 2A, 2B) can be adhered to. The probe biomolecule 30 can selectively bind a target biomolecule 30, e.g., an antibody probe and antigen target. The biomolecular probe 30 is adhered to at least one of the electrodes 14, and preferably multiple electrodes 14, so as to coat same and impart a biochemical quality to the circuit C. Methods for adhering biomolecular probes to electrodes are discussed in greater detail, below.

In a preferred embodiment, at least one electrode 14 is constructed of chromium. Alternative electrodes can be constructed of iridium, gold or similar metals. As well, a metal electrode can be plated with gold, chromium or other preferred metal.

The biomolecular probe includes a complexing biomolecule. Exemplary complexing biomolecules include proteins (e.g. an antibody), carbohydrates, lipids, hormones and other biomolecules capable of forming a complex with another moiety.

Figure 3:
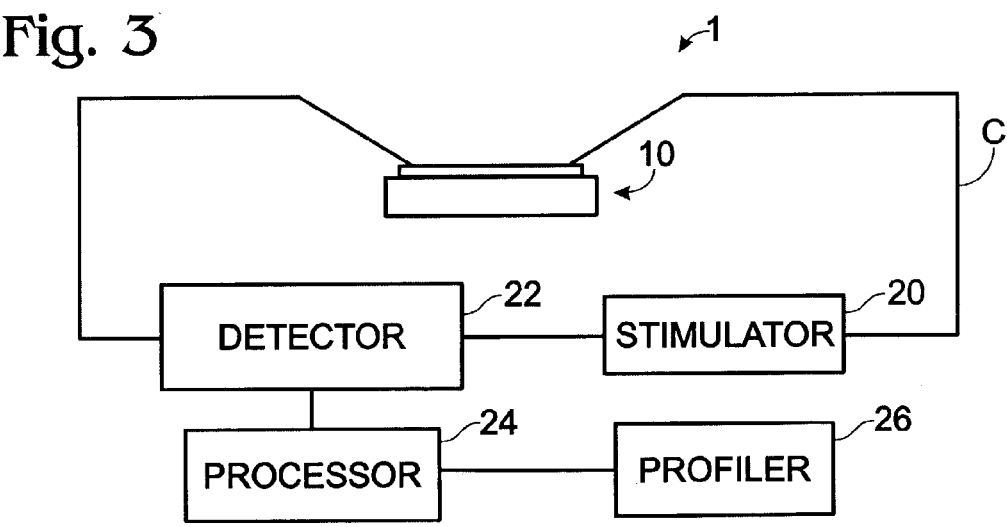
FIG. 3 diagrams a first embodiment of a device for the direct electrical detection of molecule—molecule interactions.

The bioelectrical circuit analyzer 1 of FIG. 3 further can have a stimulator 20 electrically coupled to the circuit C. The stimulator 20 is operative to provide an input alternating signal spanning a selected frequency range $F_1$–$F_2$. The selected frequency range $F_1$–$F_2$ can span a range of about $10^{-6}$ to $10^6$ Hz or higher. In preferred embodiments $F_1$ is equal to or less than about $10^{-2}$ Hz or $10^{-3}$ Hz. The high-frequency boundary $F^2$ of the selected frequency range $F_1$–$F_2$ preferably can be equal to or greater than about $10^{-4}$ Hz. The stimulator 20 and detector 22 can be provided by a single, combined test instrument (e.g., an impedance analyzer as discussed below).

A detector 22 can be coupled to the circuit C. The detector 22 is structured to detect and measure any one or more of a plurality of electrical parameters of the circuit C over the selected frequency range $F_1$–$F_2$. Parameters include phase, amplitude, dissipation factor, conductance and/or impedance.

By analysis of the detected electrical parameter(s), the detector 22 further can generate an input signal profile for a given biochemical circuit, preferably digitized across the frequency range $F_1$–$F_2$. The signal profile is a unique "electro-fingerprint" of the tested biochemical circuit, based on electrical parameter measurements at a plurality of points through the selected frequency range $F_1$–$F_2$.

The bioelectrical circuit analyzer 1 can include a comparator 24 (e.g., a suitably programmed digital processor as shown in FIG. 3) operative to compare the digitized output signal profile with a first digitized reference signal profile to detect a match across the frequency range. Signal profiles produced by the analyzer 1, as well as reference signal profiles, can be stored in a database accessible by the analyzer.

The comparator 24 further can be operative to detect a complexing event of the probe biomolecule 30 and an unknown biomolecular target 32 in the fluid test sample introduced into the sample well 12. This detection can be made on the basis of differences in the bioelectrical properties of the circuit. The biomolecular basis for fingerprinting, signal profile comparison, and detection of biocomplexes is addressed more fully below.

Figure 2A:
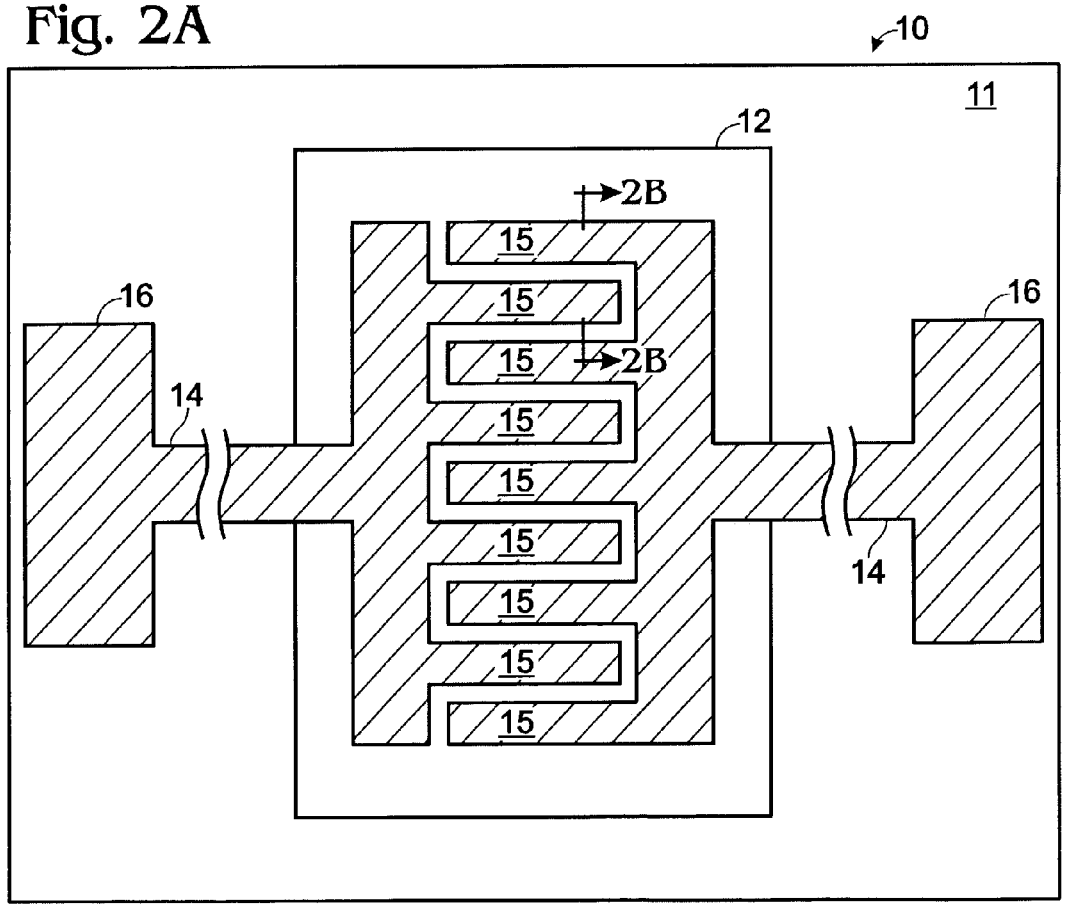
FIG. 2A is an enlarged top view of the module of FIG. 1, showing interdigitated electrodes in a sample well on a substrate.
Figure 2B:
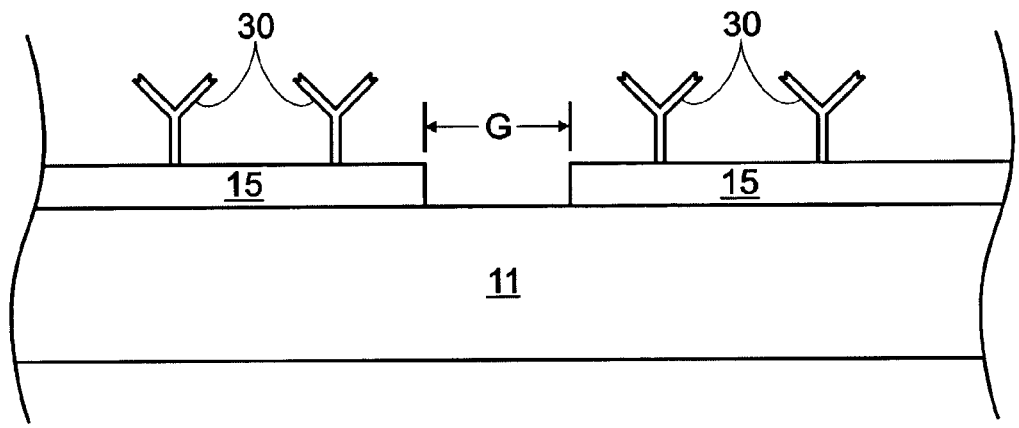
FIG. 2B is an enlarged cross-sectional view taken along line 2B—2B in FIG. 2A, showing electrode fingers with probe biomolecules adhered thereto.
Figure 2C:
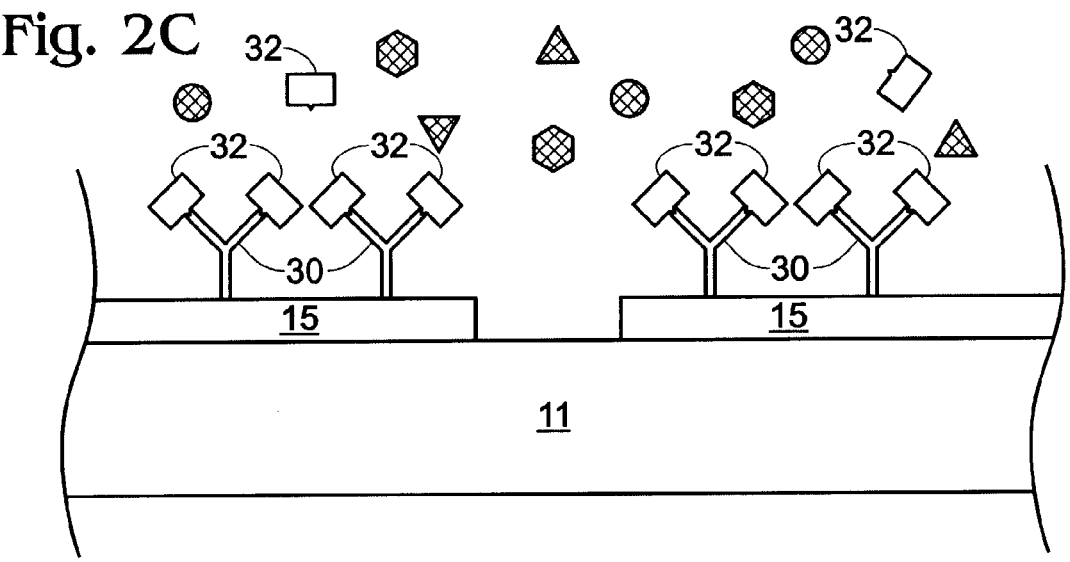
FIG. 2C is an enlarged cross-sectional view similar to FIG. 2B, showing target biomolecules bound to the probe biomolecules adhered on electrode fingers.

The metal electrodes 14 are shown in greater detail in FIG. 2A. In this representative embodiment, interdigitated electrode fingers 15 are 1000 um long, 1–5 um wide, and separated by a gap of 1–5 um. Dimensions of metal electrode fingers 15 can be varied without departing from the essential structure and function of the test cell disclosed herein.

The number of interdigitated electrode fingers 15 also can be varied. Prototype embodiments have incorporated from 100 to 500 electrode fingers 15, although a greater or lesser number can be efficaciously employed.

To manufacture a representative test cell, a 2 um oxide layer was grown on a silicon substrate 11. Next, one or more wells 12a–12n were etched in an oxide layer on the surface of the silicon substrate 11 (in an illustrative embodiment, wells are 4 mm×4 mm×1 um deep).

A high purity metal layer of 1.0 um thickness was then deposited on the substrate 11 (e.g., by using a sputtering machine). The interdigitated electrodes 15 were formed by first patterning (for example, using photolithography) and then etching off the unwanted metal layer so that the electrodes are formed in the well 12. Contacts for interdigitated electrodes 15 can be structured such that the contact pads 16 are positioned outside the well 12 (FIG. 1).

Figure 4A:
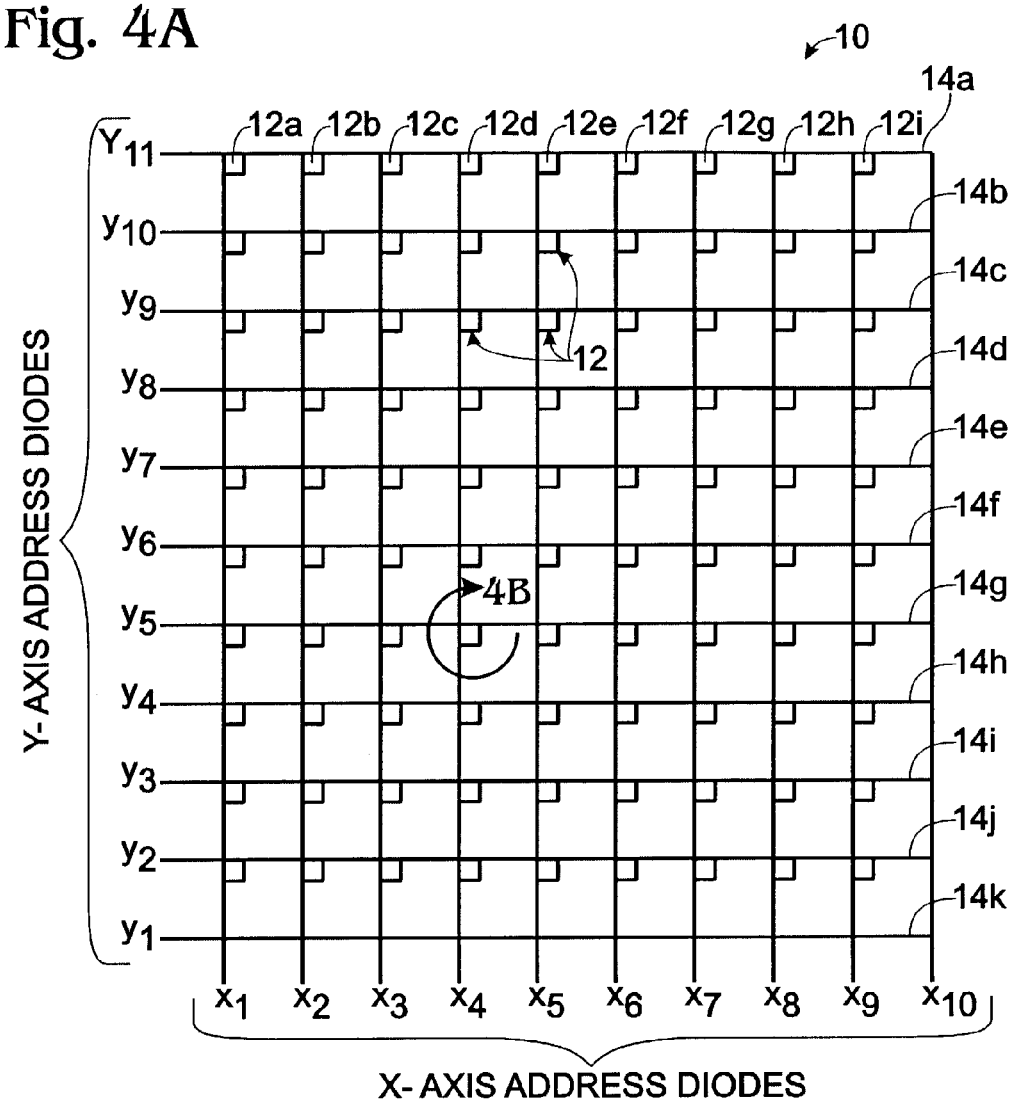
FIGS. 4A–4B are diagrams of an embodiment having a plurality of interdigitated electrode pairs arrayed on a chip.
Figure 4B:
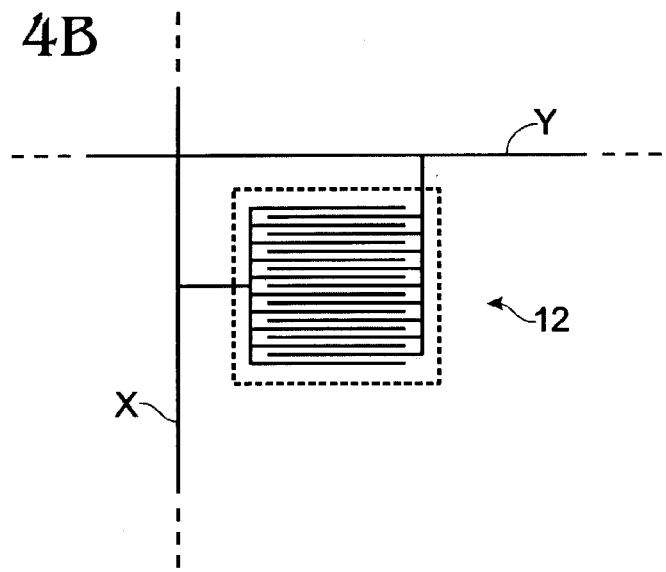

In other embodiments, shown in FIG. 4A, the bioelectrical circuit analyzer 1 can further include a plurality of sample wells 12a–12n formed on the substrate 11 and structured to receive a corresponding plurality of fluid test samples. A corresponding plurality of electrodes 14a–14n can be arranged in an X-Y array to place an electrode in contact with each sample well.

Selection circuitry (X- and Y-axis addressing) connected to the electrode contact pads 16 (FIG. 2A) is useful in these embodiments to allow a signal to be transmitted to a selected electrode. Selection circuitry can be built into a device portion of a silicon substrate 11. Contact pads 16 then can be coupled directly to the selection circuitry or other device region of the substrate 11.

In another alternative embodiment, a plurality of wells 12a–12n and interdigitated electrodes 15 can be manufactured in an array (FIG. 4A). In such a sensor array, different probe biomolecules 30 can be attached to interdigitated electrodes 15 in different sample wells 12 formed on module 10.

Using this approach, a wide range of intermolecular interactions can be simultaneously characterized in one bioelectrical circuit analyzer 1. Each set of electrodes 14 can be analyzed with its corresponding $X_n$ and $Y_n$ contact pads 16, disposed along the edge of the substrate 11 as shown. Arrayed contact addressing is similar to that used in flat panel display technology.

Adherence of Probe Biomolecules

A representative method is presented for adherence of probe biomolecules to metal electrodes 14 of an analyzer 1, such as described above. The electrodes 14 of this example are composed of chromium.

A probe biomolecule was selected, e.g. a mouse IgG monoclonal antibody directed against anti-human interferon-gamma. A small volume (e.g., 200 ul) of monoclonal antibody solution was placed in a coating buffer is contacted with the interdigitated electrodes 15 of the analyzer 1. Incubation time for attachment can be varied. Experiments have shown that an incubation period as brief as 2 minutes is effective. After incubation, the well 12 is washed.

To assess adherence of the antibody to the electrodes 14, the above method was performed using a biotin-conjugated antibody (2-minute incubation), followed by a standard calorimetric assay. For comparison, the monoclonal antibody (mAb) probe biomolecules also were bound to a conventional plastic microtiter plate, as is commonly done in ELISA assays.

The well 12 was incubated for 20 minutes with streptavidin-conjugated horseradish peroxidase (HRP). An HRP substrate, 3,3',5,5'-tetramethylbenzidine (TMB), was then added and color allowed to develop for 2 minutes before the reaction was stopped. The test solution was then transferred from the chip surface or fastwell to a microtiter plate well and assessed for absorbance at 450 nm.

TABLE 1

| Chip surface/Electrode Composition | Net O.D. (corrected) |
|---|---|
| Si/Cr | 1.344 |
| Plastic Microtiter Plate (mAb-coated) | 1.300 |
| Si/Au | 1.143 |
| $SiO_2$/— | 0.167 |
| Si/Al | 0.079 |

Results of the calorimetric assay are presented in Table 1. These data indicate that antibodies were attached to the Si/Cr embodiment better than to most other tested electrode compositions. A chromium electrode proved most efficacious in binding antibody as compared with aluminum and $SiO_2$. High binding efficiency was observed for the chromium electrode, on a par with that of plastic microtiter ELISA plates. Binding to gold was acceptable but not as optimal as that to chromium.

It should be noted that, for the Si/Au electrode, the integrity of the gold electrode was suboptimal, with peeling of the electrode from the surface of the substrate 11 seen when aqueous buffers were added. The gold surface was stabilized when gold was coated over a chromium electrode base.

Data further indicate that approximately twice as much antibody was bound to a Si/Ir chip as compared to the Si/Cr chip. Unfortunately, the iridium electrode was observed to have a background reactivity (with the enzyme alone) of roughly three times that of chromium.

The antibody concentration was titrated to determine the sensitivity of detection using the above-described 2-minute probe biomolecule adherence protocol. Antibody solutions were made up using 6 dilutions: 2,000 ng/ml, 400 ng/ml, 80 ng/ml, 16 ng/ml, 3.2 ng/ml, and 0.64 ng/ml. These dilutions resulted in net O.D. readings of 0.763±0.065, 0.627+0.110, 0.317±0.021, 0.064±0.006, 0.000±0.001, and 0.000±0.013, respectively. These results demonstrate that the sensitivity of detection of the antibody was about 16 ng/ml under these conditions.

Antibody binding is increased when the adherence protocol is performed in the presence of an electrical field. An electrode was devised that allowed the substrate 11 to act as either the cathode (+polarity) or anode (−polarity). The antibody solutions, as using in the above titration assay, were placed in the sample well 12 and the electrical field applied to the solution. The electrical conditions were set at 1 mA direct current producing 2 V, and the incubation proceeded for 2 min.

TABLE 2

| Antibody Conc. (ng/ml) | Net O.D. No Field | Δ(Net O.D.) Chip as Cathode | Δ(Net O.D.) Chip as Anode |
|---|---|---|---|
| 2,000 | 1.221 | +0.269 (+22%) | −0.025 (−2%) |
| 400 | 0.840 | +0.200 (+24%) | — |
| 80 | 0.305 | +0.086 (+28%) | +0.025 (+8%) |
| 16 | 0.076 | +0.114 (+150%) | Precipitated (0%) |

The results of these experiments, using different concentrations of antibody, are summarized in Table 2. These results indicate that the antibody binding is enhanced when the chip is positively charged, especially at lower protein concentrations. No additional binding was observed when the chip is negatively charged; in fact, a negative charge proved non-optimal in some cases.

The use of a field with the substrate 11 as cathode therefore can be beneficial in depositing low concentrations of probe biomolecules 30 onto the electrodes 14. The sensitivity of detection of antibody with the substrate 11 as cathode (<16 ng/ml) is equivalent to 100 pM antibody.

It is hypothesized that the presence of an alternating electric field orients probe molecules differently on the electrode surface than in a static state. By way of example, antibodies are non-symmetric molecules; hence their polarization and their dielectric behavior will change when subjected to an alternating input signal. The above variation of the probe binding method (application of electric field during adherence incubation) allows an additional parameter for electrically detecting molecules and molecule—molecule interactions.

The antigen, in this example anti-human interferon-gamma to which the mouse IgG monoclonal antibody was directed, was then added in each of two sample wells: a first sample well 12 with bare metal electrodes and a second well having an antibody-coated electrode. The MOPS buffer was used to provide an acceptable chemical environment for antibody-antigen specific binding.

Detection Methodology in General

The capacitance, dissipation factor, phase, conductance and/or impedance, measured over the selected frequency range for the antibody-coated electrode, antibody-coated electrode with antigen in solution above, and biomolecular complex adhered to the electrode, therefore can provide unique fingerprints of these molecules and molecule—molecule complexes.

The electrical character of the electrodes 14 of the biochemical circuit C can be electrically altered by an electro-molecular change in the probe 30 or probe 30-target 32 complex adherent thereto. The change in electro-molecular properties is caused by an applied signal of changing frequency provided by a stimulator 20.

The measured electrical parameters are based on the fact that the molecules investigated are relatively large and are therefore believed to affect the dielectric value and the conduction of current across the electrode gap.

The variable in the above example is the frequency of the alternating input signal. When an electric field is applied across a molecule, there is a tendency for the charges on the molecule to align with this applied field. In larger molecules, the electron cloud surrounding these molecules often redistributes; hence, there is some charge separation or molecular polarization.

The ability and rapidity of molecular charge separation depends on the strength of the covalent and electrostatic bonds. Loosely-bound charges can respond to the electric field at higher frequencies (e.g., $10^2$ to $10^5$ Hz); similarly, tightly-bound charges respond to the electric field at lower frequencies (e.g., $10^{-4}$ to $10^0$ Hz). Thus, by looking at the response over a frequency range, specific traits of a given molecule (or biomolecular complex) can be examined.

The present approach can be carried out by examination of one or more electrical parameters. It can be anticipated that, for large biomolecules displaying gross changes to changing frequency inputs, a single parameter may be sufficient to perform identification. For smaller biomolecules or those exhibiting more subtle electro-signatures, a plurality of electrical parameters preferably are examined.

The applied field between the electrodes will transport a signal between them. The transfer of charge between the electrodes across the gap will be affected by the molecules attached to them. Consequently, the resistance or impedance behavior exhibited by the signal will depend on the attached molecules and can be observed in the electrical parameter scan.

A capacitance scan permits examination of the dielectric response, which was observed to become dominant at lower frequencies. The dissipation factor indicates the ratio of resistance to capacitive reactance between the electrodes. Impedance or resistance also will induce a phase difference between the applied voltage and the current. This phase difference also can be measured.

A method for generating a signal profile for a biomolecule or biomolecular complex entails first adhering a biomolecule, e.g. probe biomolecule 30, on an electrode 14 positioned on the conductive substrate 11.

An alternating input signal is applied to the electrode having probe biomolecules adherent thereon. The input signal includes a frequency range of from greater than $10^{-6}$ Hz to about $10^6$ Hz and preferably is an alternating current.

Signal parameters are measured over the frequency range for a plurality of electrical parameters of the electrode having a probe biomolecule adherent thereon. The plurality of electrical parameters can include capacitance, phase, dissipation, conductance and/or impedance. In preferred embodiments, the electrical parameters include all four of capacitance, phase, dissipation factor and impedance.

The measured signal parameters over the frequency range for the coated electrode are stored as a probe biomolecule electrical parameter profile. The parameter profiles can be stored in a database, memory or other means. Parameter data can be measured over a frequency range that is about two orders of magnitude within the selected frequency range, and further can be logically associated with the biomolecule.

The method can further include forming a biochemical complex on the electrode 14 on the conductive substrate 11. The complex is formed by the probe biomolecule 30, which has been adhered on the electrode, and a target biomolecule 30 introduced into the sample well 12.

The biochemical complex can contain as one member a protein, such as an antibody or a glycoprotein; a hormone; a gene transcription regulating component; a polynucleotide; a carbohydrate; an immune system component; or other relevant biomolecule capable of complexing. For example, a specific DNA sequence (i.e, probe biomolecule) can be adhered to the electrode 14 and a gene transcription regulating protein introduced to the sample well 12. The regulating component (i.e., target biomolecule) can bind to the adhered DNA sequence.

The pattern of electrical parameter changes further can be used to correlate the measured pattern of electrical parameter changes with a specific biomolecular species in the liquid sample. Such correlation can be used to detect and identify a specific target in a sample using a test cell having a plurality of different probes attached to the electrodes thereof.

Generation of Reference Set

A reference set can be created, wherein each reference profile in the set is a profile of reference electrical parameter changes for a biochemical species. A generated sample profile can then be compared to the members of the reference set. Because of the unique stereochemical structure of the probe, target, and probe-target complex, as well as the electron distribution therein, the profile observed for a particular probe-target complex is sufficiently distinctive that it can be used to identify that complex.

A method for generating a biomolecule electrical parameter profile database can proceed similarly. After adhering a probe biomolecule on an electrode positioned on a conductive substrate, an alternating input signal is applied to the circuit. The input signal includes a frequency range of from greater than $10^{-6}$ Hz to about $10^6$ Hz.

Signal parameters are measured over the frequency range for a plurality of electrical parameters of the electrode in the circuit, the electrical parameters including capacitance, phase, dissipation factor and impedance.

Measured signal parameters over the frequency range are stored as a probe biomolecule electrical parameter profile.

A reference profile for the bare metal electrode 14 can also be generated, by applying an alternating input signal to an electrode free of adherent probe biomolecules, and measuring and storing same as an electrode electrical parameter profile.

In scaling up, a $2^{nd}$–$n^{th}$ probe biomolecule can be adhered on a corresponding $2^{nd}$–$n^{th}$ electrode positioned on at least a first conductive substrate. Similarly, an alternating input signal then can be applied to the $2^{nd}$–$n^{th}$ electrode, the input signal including a frequency range of two or more orders of magnitude selected from greater than $10^{-6}$ Hz to about $10^6$ Hz.

Measurement of signal parameters over the frequency range for a plurality of electrical parameters of the $2^{nd}$–$n^{th}$ electrode having the $2^{nd}$–$n^{th}$ probe biomolecule adherent thereon proceeds as above, the plurality of electrical parameters including capacitance, phase, dissipation factor, conductance and/or impedance. Measured signal parameters over the frequency range likewise are stored for the plurality of electrical parameters of the $2^{nd}$–$n^{th}$ electrode as the $2^{nd}$–$n^{th}$ probe biomolecule electrical parameter profile.

The reference database further can contain one or more probe-target bio-complex electrical parameter profiles. As described above, introduction of a target biomolecule into the sample well can form a bio-complex with the probe biomolecule on the electrode.

Additionally, a $2^{nd}$–$n^{th}$ target biomolecule can be introduced to form a $2^{nd}$–$n^{th}$ biomolecular complex with the $2^{nd}$–$n^{th}$ probe biomolecule on the $2^{nd}$–$n^{th}$ electrode prior to applying the alternating input signal to the $2^{nd}$–$n^{th}$ electrode. Measured signal parameters over the frequency range are stored for the plurality of electrical parameters as the 2nd-$n^{th}$ target biomolecule electrical parameter profiles.

Method Applied to Examples

A method is disclosed for analyzing a biochemical circuit having a liquid sample in contact with two interdigitated electrodes, wherein at least one of the electrodes has probe biomolecules adhered thereto. The method includes contacting the sample with an electrode in a sample well formed on a conductive substrate, thereby form a biochemical circuit.

An alternating input signal spanning a selected frequency range $F_1$–$F_2$ is applied to the circuit and an output electrical parameter of the biochemical circuit is measured over the frequency range, particularly any change in response to the change in frequency.

A test sample profile can be generated from the measured electrical parameter and used to correlate the test sample profile to a reference profile in a database or set of reference profiles.

The test sample profile can be generated by creating a plurality of data pairs, wherein each pair includes a frequency of a discrete input signal and a measured output electrical parameter for that discrete input signal. The plurality of data pairs can be associated with the unknown component in the liquid sample, and the associated data pairs stored.

Identification of an unknown component can be accomplished by comparison of the generated sample profile to at least a portion of a plurality of reference profiles in a reference profile database. The plurality of reference profiles can include reference profiles of a known receptor-ligand complexes, non-complexed receptors of known receptor-ligand pairs, non-complexed ligands of known receptor-ligand pairs, or a combination of these types of reference profiles.

Results are presented below in which a representative method was undertaken using antibodies and their respective antigens. A sweeping frequency spanning about $5 \times 10^1$ Hz to $10^7$ Hz was applied to the bound antibody alone (probe biomolecule), bound target molecule or control molecule alone (target biomolecule), and to a target molecule solution applied to a test cell having antibody bound thereto (probe and target biomolecules, expected to join and form a bio-complex).

First, a drop (~50 ul) of dilute buffer solution (e.g., 0.1 M MOPS) was placed in a sample well. Electrode tips were contacted with the contact pads of an interdigitated pair of chromium electrodes. An alternating current input signal was applied to the solution in the well (e.g., using an HP4192A Impedance Analyzer (Hewlett-Packard, Denver, Colo.) or a Solartron 1260 Impedance Analyzer (Solartron, San Diego Calif.)), varying in frequency from 5 Hz to 13 MHz.

Background electrical parameters (capacitance, dissipation factor, impedance (or conductance) and phase) were recorded and an electrode reference profile produced. The buffer solution was removed and the well rinsed.

A drop of a solution containing anti-dinitrophenol (DNP) murine IgG was then placed in the sample well. The antibodies were incubated for 1–5 minutes, during which time the antibodies were adhered to the chromium electrodes.

Impedance, phase, dissipation, and capacitance frequency spectra of an antibody-coated test cell were then measured according to the methods described above. The detector used for these experiments again was an HP4192A Impedance Analyzer and Solarton 1260 Impedance Analyzer.

Two DNP-tagged target molecules (DNP-albumin and DNP-serine) and a control molecule (d-biotin) were used as target biomolecule in assays on an antibody-coated chromium electrode as described above. Phase and conductance data of the assays are shown in FIGS. 5–8. In each case, data were normalized to remove effects of the sample well and buffer.

Figure 5:
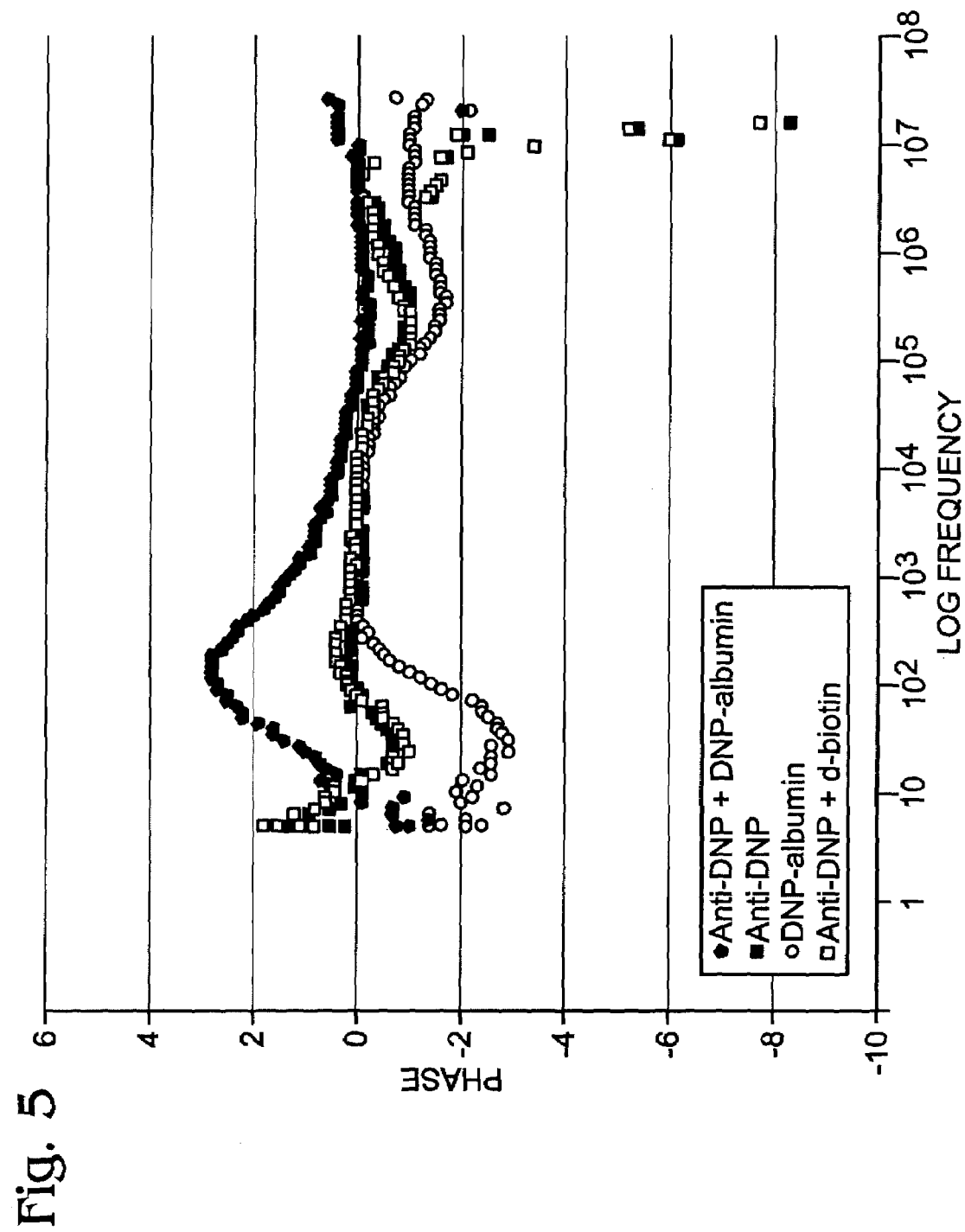
FIGS. 5–8 are graphs presenting experimental results for an antibody-antigen pair, generated using an analyzer device and method as described herein.
Figure 6:
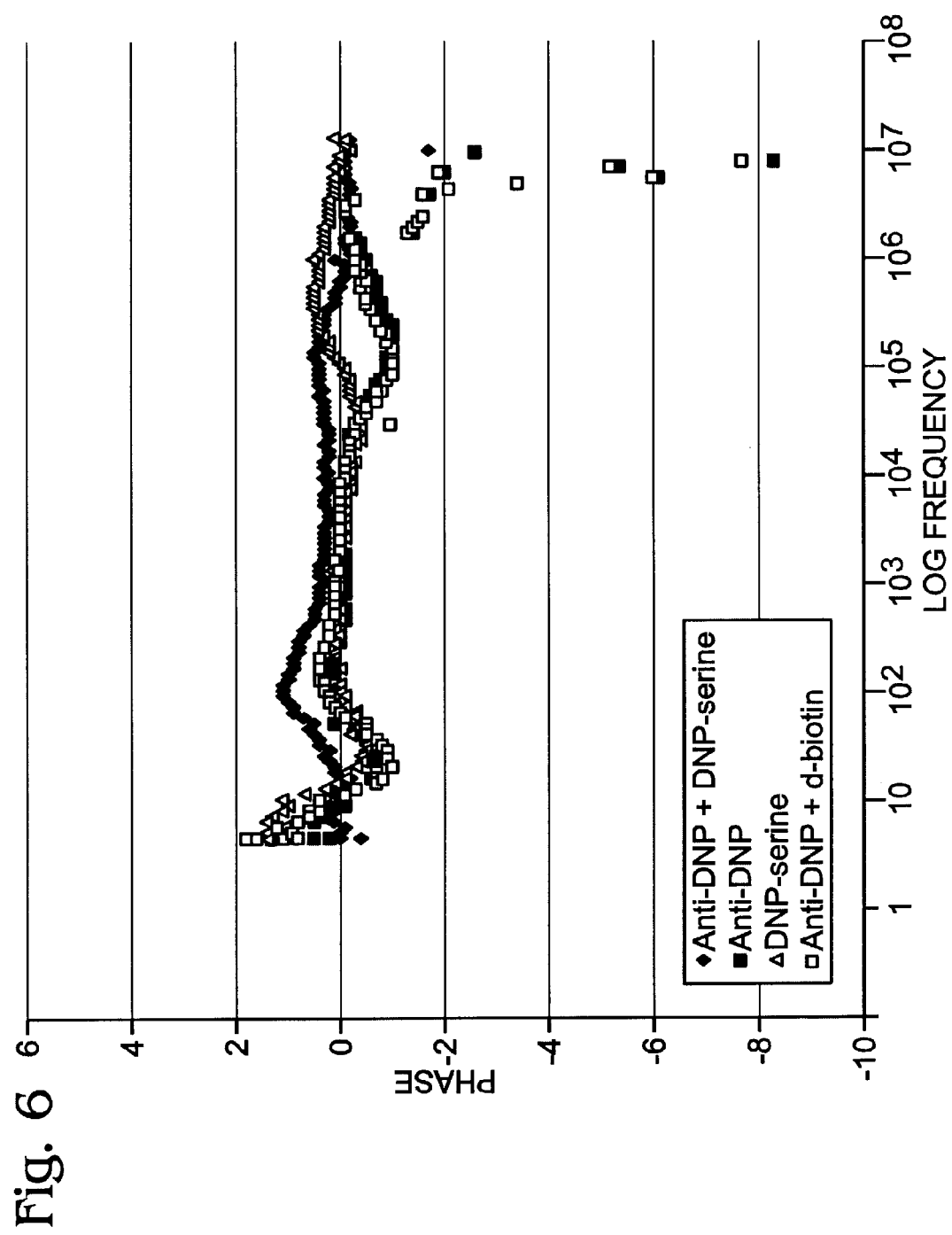

FIGS. 5–6 present phase data for anti-DNP IgG with, respectively, DNP-albumin and DNP-serine in the fluid test sample. The phase parameter is the phase difference, in degrees, between the current and voltage that occurs in a non-passive circuit. It can be seen that phase for each molecule varies with frequency, indicating that molecules are behaving as reactive components in the circuit. A zero phase difference implies that the molecules act passively in the circuit.

The antibody/DNP-albumin target complex (open pentagon) can be clearly distinguished from bound antibody alone (black square), free DNP-albumin target (open circle) and free d-biotin control target (open square) by differences in phase, and especially over the range of 10–100 Hz.

The phase data indicates that the antibody/target complex acts as an electrically different molecular structure than bound antibody and free target in solution. Note that the line representing incubation of bound anti-DNP antibody with d-biotin (open square) does not have a distinctive peak at about 100 Hz, indicative of antibody specificity.

A second target molecule, DNP-serine, was used in related experiments (FIG. 6). Similarly to the results with DNP-albumin, a distinctive phase peak was observed at about $10^1$–$10^3$ Hz (open diamond). A second peak occurred at $10^4$–$10^6$ Hz. This latter variation is absent from the data shown in FIG. 5 (compare to open pentagon).

When anti-DNP IGG alone is bound to the test cell electrode, it can be seen to yield consistent phase data (compare FIGS. 5–6). Conversely, DNP-albumin and DNP-serine are observed to produce readily distinguishable plotted phase curves.

Figure 7:
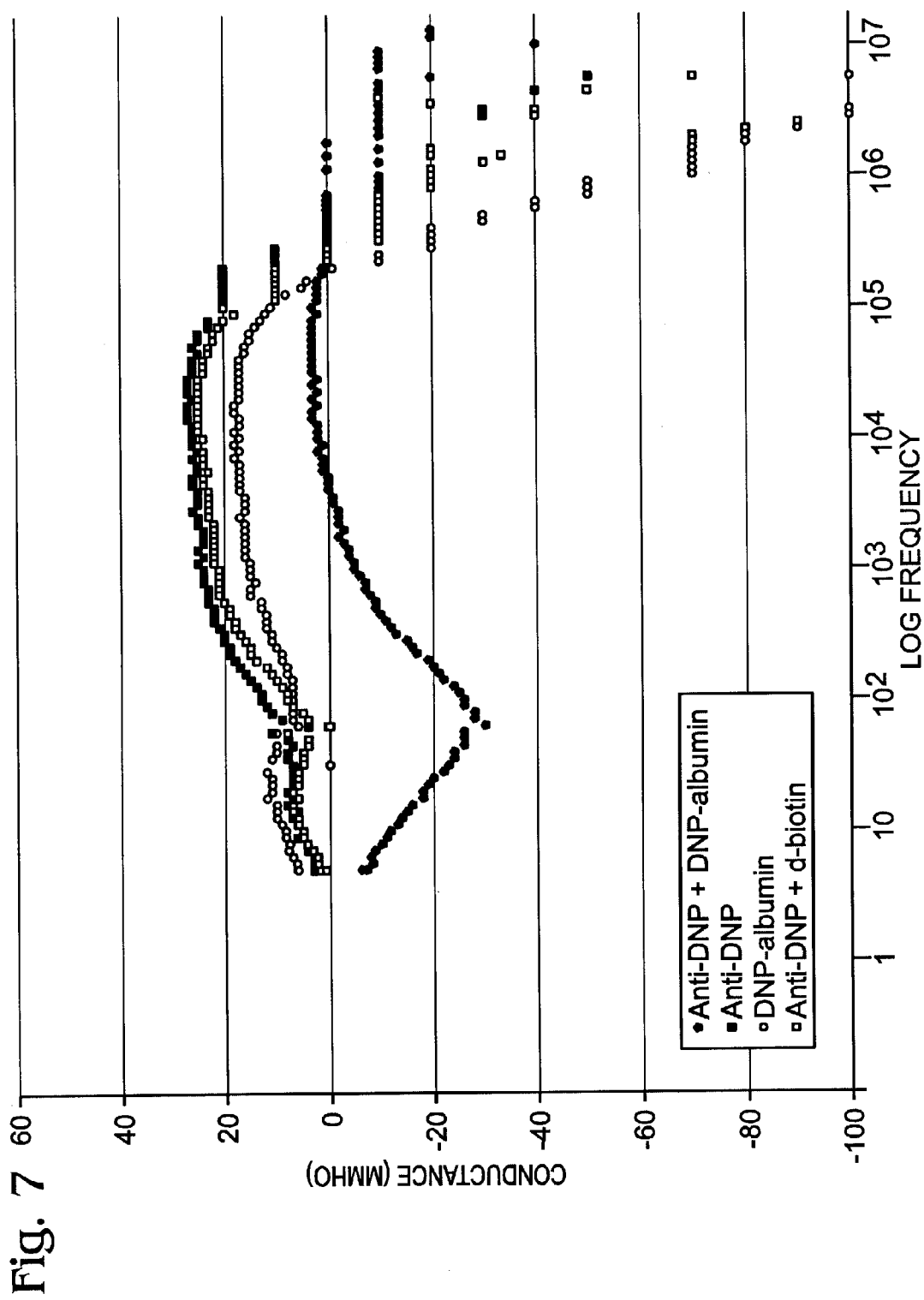
Figure 8:
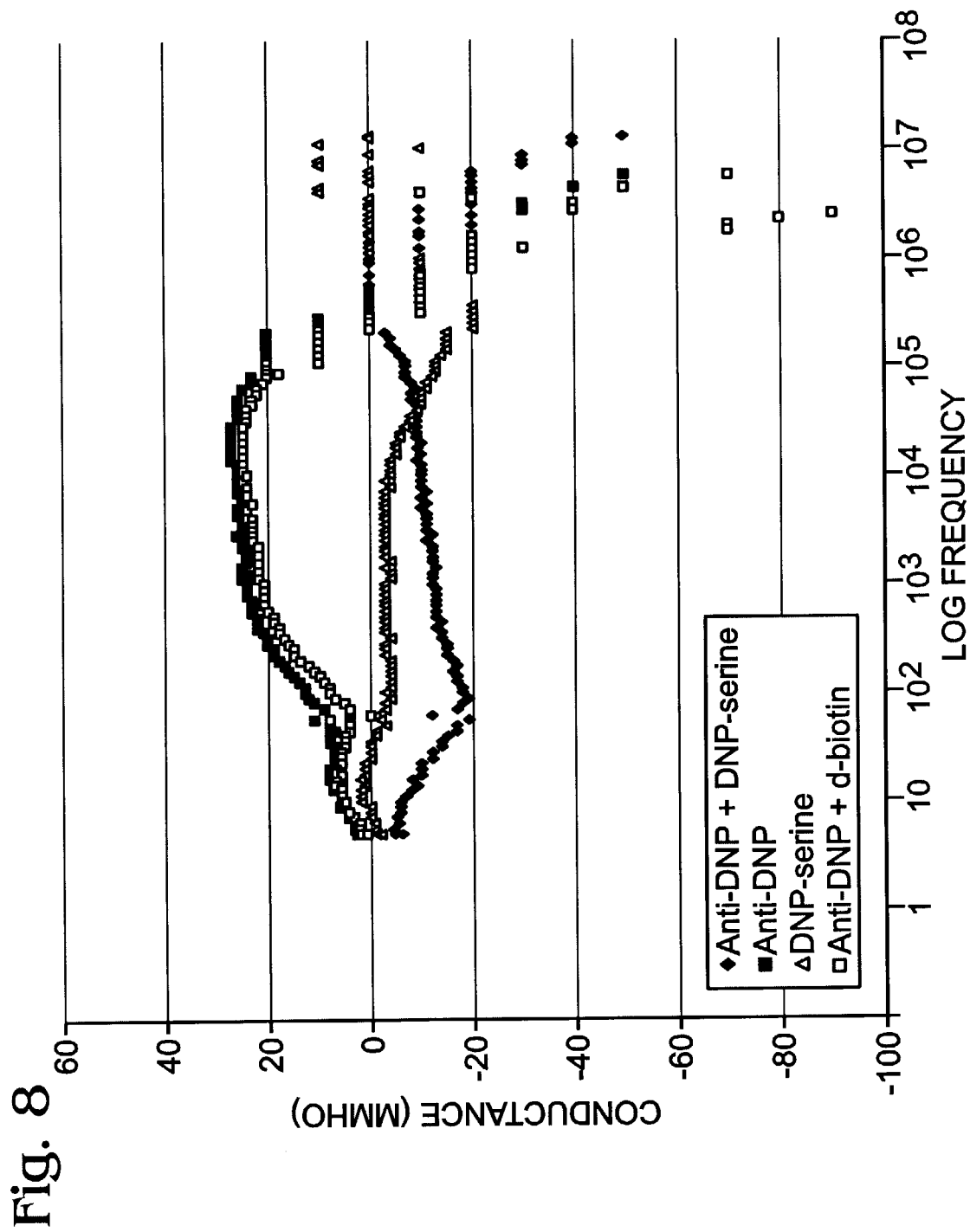

Conductance data for the above target biomolecules are shown in FIGS. 7–8. The change in conductance of an test cell when anti-DNP IgG antibody bound its DNP-albumin target is clearly seen by a characteristic dip at about 90 Hz and a slight dip at about $10^7$ Hz (FIG. 7).

The line representing antibody/biotin control (open square) closely matches that for bound antibody alone (black square), indicating that biotin remained free in solution and had little effect on the conductance of the circuit.

It is important to note that the conductance plot of anti-DNP IgG/DNP-serine complex bear gross similarity to that of anti-DNP IgG/DNP-albumin. However, the two curves can be differentiated based on the strength and shape of the dips at about $10^2$ Hz and about $10^6$ Hz.

It should further be appreciated that the phase and conductance data for anti-DNP IgG, whether alone or in the presence of d-biotin, are very nearly identical in all the experiments. This uniformity in electrical response occurred despite differing biomolecular milieu in the test sample solutions above the antibody-adhered electrode. As well, DNP-albumin and DNP-serine can be easily discriminated in the both phase and conductance plots.

The uniform and repeatable electrical response of the probe biomolecule, combined with the unique "electrofingerprint" of various target biomolecules, facilitates diagnostic as well as quantitative applications.

The device and method can be used to assay patient fluid samples for the presence of a variety of substances. Tests can be performed to detect, for example, HIV sero-conversion or exposure to Varicella-Zoster or hepatitis viruses.

In addition, an antibody probe can be employed to detect and identify a microorganismal target moiety. Exemplary target microorganisms include, e.g., *Neisseria meningitidis, Streptococcus pneumoniae*, or *Haemophilus influenzae* (bacterial meningitis); anthrax; smallpox; and differentiation of gram-negative and gram-positive bacteria.

Environmental samples similarly can be assayed to detect contamination levels in water supplies and other locations, including natural contamination and artificially-introduced contaminants (e.g., pollution, anthrax or smallpox as a result of terrorism).

For example, a probe molecule can be employed that specifically binds lead ions; electro-molecular changes induced by ion binding can be detected by the analyzer and used to determine the presence of lead in a sample.

It should be further apparent that the device and method disclosed herein are not limited to the representative antibody-antigen complexes presented. Indeed, the device can readily be used to detect interactions of other molecular species. For example, protein—protein interactions can be assessed with no significant change to the device or method.

As well, other molecular milieu can be assayed using a device and method as disclosed herein. For example, deoxyribonucleic acids have been successfully bound to the above-disclosed device using the method herein disclosed. In one technique, a binding anchor was joined to one end of a DNA strand, such that the DNA strand could be adhered to the electrode with the bulk of the DNA bases remaining free in the solution (i.e., the strand adhered only at one end). The specific sequence of the DNA strand therefore is available for hybridization to a complementary target strand. The present device therefore can be utilized in electrical characterization of annealed nucleic acid duplexes.

Moreover, the present test cell, device and method need not be limited to use with biological molecules, but can be used to detect aerosol or soluble chemical moieties, such as a toxic gas or evaporated acid, by the effect of such moiety on an appropriately selected probe on the test cell.

Another feature of the present analyzer is the ability to train a neural network with the target biomolecule electrical parameter profiles. Once the frequency scans of the plurality of parameters are recorded, this data is fed to a neural network that will identify and store distinctive data features. When an unknown molecule is subsequently analyzed, its response will be compared to the stored data to identify it and/or determine its interaction with or relationship to the known molecule adhered to the electrodes.

A person skilled in the art will be able to practice the present invention in view of the description present in this document, which is to be taken as a whole. Numerous details have been set forth in order to provide a more thorough understanding of the invention. In other instances, well-known features have not been described in detail in order not to obscure unnecessarily the invention.

While the invention has been disclosed in its preferred form, the specific embodiments and examples thereof as disclosed and illustrated herein are not to be considered in a limiting sense. Indeed, it should be readily apparent to those skilled in the art in view of the present description that the invention can be modified in numerous ways. The inventor regards the subject matter of the invention to include all combinations and sub-combinations of the various elements, features, functions and/or properties disclosed herein.

The invention claimed is:

1. A bioelectrical analyzer for identifying a biomolecular target comprising a protein or peptide, the analyzer comprising:
    a silicon substrate;
    a sample well formed on the substrate and structured to receive a fluid test sample;
    an electrode formed within the sample well of a metal having an exposed chromium surface to which proteins and peptides are directly adherent and the chromium surface having adherent thereto a biomolecular probe capable of complexing with a biomolecular target, the biomolecular probe comprising a protein or a peptide;
    a stimulator electrically coupled to the electrode and structured to provide an input signal spanning a selected frequency test range $F_1$–$F_2$ within the frequency range;
    a detector operative to detect a signal of the fluid test sample over the selected frequency test range and generate a sample signal profile for at least one sample electrical parameter across the selected frequency test range; and
    means for comparing the sample signal profile with a first reference signal profile to detect a match across the selected frequency test range.

2. The bioelectrical analyzer of claim 1 wherein the test sample includes an unknown biomolecular target comprising a protein or a peptide, and the means for comparing is operative to detect a complexing event of the probe and target.

3. The bioelectrical analyzer of claim 1 wherein $F_1$ is equal to about $10^{-2}$ Hz.

4. The bioelectrical analyzer of claim 1 wherein $F_2$ is equal to or less than about $10^6$ Hz.

5. The bioelectrical analyzer of claim 1 wherein $F_2$ is equal to or less than about $10^3$ Hz.

6. The bioelectrical analyzer of claim 1 wherein $F_1$ is less than $10^2$ Hz.

7. The bioelectrical analyzer of claim 1 wherein the sample electrical parameter includes dissipation factor.

8. The bioelectrical analyzer of claim 1 wherein the detector is operative to detect a plurality of sample electrical parameters over the selected range of frequencies, the plurality of electrical parameters including phase and dissipation factor.

9. An electrode module according to claim 1 in which the substrate comprises a silicon substrate having a layer of silicon insulative layer in which the sample well is formed, the chromium electrodes being formed on the silicon insulative layer within the sample well.

10. An electrode module for use in a bioelectrical circuit analyzer for identifying biomolecular target molecules comprising a protein or a peptide, comprising:
    a silicon substrate;
    a sample well formed on the substrate and structured to receive a fluid test sample; and
    a circuit element including chromium electrodes in contact with the sample well and having an exposed chromium surface, the surface having adherent thereto a biomolecular probe comprising a protein or peptide.

11. The electrode module of claim 10, further comprising a silicon oxide layer between the silicon substrate and the chromium electrode.

12. The electrode module of claim 10 wherein the chromium surface of the electrode is coated with the biomolecular probe.

13. The electrode module of claim 10 wherein the biomolecular probe includes a complexing biomolecule.

14. An electrode module according to claim 10 in which the substrate comprises a silicon substrate having a layer of silicon insulative layer in which the sample well is formed, the chromium electrodes being formed on the silicon insulative layer within the sample well.

15. An electrode module for a bioelectrical circuit analyzer for identifying proteins and peptides, the module comprising:
    a silicon substrate;
    a sample well formed in the substrate and structured to receive a fluid test sample;
    a pair of electrodes formed in the sample well in opposed spaced-apart relationship to receive the test sample between the electrodes; and
    means for coupling the electrodes to a stimulator to apply an electrical signal to the electrodes and sample and to a detector operative to detect an electrical parameter of the signal applied to the sample;
    the electrodes comprising chromium having an exposed surface so that a protein or peptide is adherent directly to the electrodes.

16. An electrode module according to claim 15 in which the electrodes are formed in an interdigitated relationship.

17. An electrode module according to claim 15 in which probe molecules comprising the protein or peptide are adhered directly to the electrodes.

18. An electrode module according to claim 17 in which the probe molecules consist essentially of antibodies.

19. An electrode module according to claim 17 in which the probe molecules consist essentially of antigens.

20. An electrode module according to claim 15 in which the substrate comprises a silicon substrate having a layer of silicon insulative layer in which the sample well is formed, the chromium electrodes being formed on the silicon insulative layer within the sample well.

21. An electrode module according to claim 20, including a plurality of said sample wells, each containing a pair of said electrodes, the electrodes of each well being coupled to selection circuitry for connection to the stimulator and detector.

* * * * *